(12) United States Patent
Knezek et al.

(10) Patent No.: US 12,409,008 B2
(45) Date of Patent: Sep. 9, 2025

(54) NEGATIVE PRESSURE RESPIRATORY TREATMENT HOOD SYSTEM

(71) Applicant: Hygia Health LLC, Lafayette, LA (US)

(72) Inventors: Erick Knezek, Lafayette, LA (US); Matthew Marcy, Bluemont, VA (US); Douglas Clement, Lafayette, LA (US)

(73) Assignee: HYGIA HEALTH, LLC, Lafayette, LA (US)

( * ) Notice: Subject to any disclaimer, the term of this patent is extended or adjusted under 35 U.S.C. 154(b) by 307 days.

(21) Appl. No.: 17/915,132

(22) PCT Filed: Mar. 28, 2021

(86) PCT No.: PCT/US2021/024545
§ 371 (c)(1),
(2) Date: Sep. 28, 2022

(87) PCT Pub. No.: WO2021/202319
PCT Pub. Date: Oct. 7, 2021

(65) Prior Publication Data
US 2023/0149120 A1    May 18, 2023

Related U.S. Application Data

(60) Provisional application No. 63/001,897, filed on Mar. 30, 2020.

(51) Int. Cl.
*A61B 90/40* (2016.01)
*A61G 10/00* (2006.01)
(Continued)

(52) U.S. Cl.
CPC ............ *A61B 90/40* (2016.02); *A61G 10/005* (2013.01); *A61G 10/02* (2013.01); *A61L 9/20* (2013.01);
(Continued)

(58) Field of Classification Search
CPC ........ A61B 90/05; A61B 90/40; A61G 10/00; A61G 10/005; A61G 10/02; A61G 10/023; A61G 10/04
See application file for complete search history.

(56) References Cited

U.S. PATENT DOCUMENTS 4,949,714 A * 8/1990 Orr .................... A61M 16/0627
128/200.24
5,832,919 A * 11/1998 Kano .................... A61G 10/005
600/20
(Continued)

*Primary Examiner* — Keri J Nelson
(74) *Attorney, Agent, or Firm* — LAW OFFICE OF JESSE D. LAMBERT, LLC

(57) ABSTRACT

A negative pressure respiratory treatment hood for human medical patients. A rigid hood, preferably of unitary fabrication from a clear material, is positioned over the patient's head. The patient's body extends out of an opening in a front wall of the hood. A hinged door may be attached to the front wall of the hood, and is closed and partially closes the opening, and a shroud is sealing connected to the hood and is draped over the patient so as to form a pressure seal. A negative pressure source is connected to the hood and forms a negative pressure environment around the patient's head. Access openings have a resilient material across them, with small openings in the resilient material, to permit access to the patient by medical personnel and/or medical equipment.

19 Claims, 4 Drawing Sheets

(51) Int. Cl.
*A61G 10/02* (2006.01)
*A61L 9/20* (2006.01)
*A61M 16/00* (2006.01)
*A61G 10/04* (2006.01)

(52) U.S. Cl.
CPC ... *A61M 16/0003* (2014.02); *A61B 2090/401* (2016.02); *A61G 10/023* (2013.01); *A61G 10/04* (2013.01); *A61M 2016/003* (2013.01)

(56) References Cited

U.S. PATENT DOCUMENTS

| | | | | |
|---|---|---|---|---|
| 5,871,522 | A * | 2/1999 | Sentilles | A61B 90/40 |
| | | | | 607/94 |
| 6,210,320 | B1 * | 4/2001 | Rogone | A61G 11/00 |
| | | | | 600/21 |
| 6,685,622 | B2 * | 2/2004 | O'Connor | A61B 90/40 |
| | | | | 422/1 |
| 7,998,125 | B2 * | 8/2011 | Weston | A61M 1/84 |
| | | | | 604/320 |
| 9,974,705 | B2 * | 5/2018 | Rapoport | A61G 10/00 |
| 10,251,801 | B2 * | 4/2019 | Breegi | A61B 90/30 |
| 2003/0130591 | A1 * | 7/2003 | Starr | A61M 16/085 |
| | | | | 600/538 |
| 2004/0255937 | A1 * | 12/2004 | Sun | A61G 10/00 |
| | | | | 128/201.25 |
| 2020/0179219 | A1 * | 6/2020 | Petersen | A61H 9/0057 |

* cited by examiner

NEGATIVE PRESSURE RESPIRATORY TREATMENT HOOD SYSTEM

CROSS REFERENCE TO RELATED APPLICATIONS

This United States non-provisional patent application claims priority to U.S. provisional patent application Ser. 63/001,897, filed Mar. 30, 2020, for all purposes. The disclosure of that provisional patent application is incorporated herein by reference, to the extent not inconsistent with this disclosure.

BACKGROUND—FIELD OF THE INVENTION

This invention relates to apparatus used in connection with medical procedures. While not confined to use with any single treatment, by way of example this invention relates to apparatus and methods used in connection with the treatment of patients which have highly contagious diseases.

It is known that in the process of treating such patients, including but not limited to intubations, frequently the patients expel contaminated aerosols or otherwise emit germs. Such aerosols, when carrying highly contagious and potentially very dangerous viruses such as that known as COVID-19, create a very dangerous situation for the health care professionals carrying out treatment. Even though the health care professionals use personal protective equipment, known by the acronym PPE, they remain at risk for contracting serious illnesses.

It is therefore desired to have an apparatus which reduces the exposure of the health care professionals to potentially dangerous aerosols, germs, etc. emitted by the patient during treatment. Current apparatus and methods all exhibit various limitations, giving rise to a desire for an improved apparatus and method that addresses these issues.

SUMMARY OF THE INVENTION

The negative pressure respiratory treatment hood system embodying the principles of the present invention comprises a rigid, generally box-shaped hood with walls and a size and shape designed to receive to receive the head, neck and a portion of the shoulders of a patient to be intubated or otherwise treated. The hood has an opening in the front wall. The patient would typically be on his/her back on a table, face up, and the hood is placed in position over the patient's body, or the patient is moved into position within the hood. A hinged door may be attached to the hood, usually near an upper edge of the opening in the front wall, and movable between a first, open position, to permit placement of the hood around the patient; and a second, closed position rotated down toward the patient's body and latched in place. If provided, the door preferably has a cut-out shape to fit the general shape of the patient's body, with a shroud, preferably of an elastic material, to fit tightly around the body and provide a seal. The shroud is fastened tightly in place to seal around the patient's body by cleats or similar fasteners, fastening it to the hood.

A plurality of access openings are provided in the walls of the hood to permit access to the interior of the hood, and thus the patient, by healthcare workers. Each opening comprises an elastic material forming a shroud or cuff, having a hole therein. When the health care worker's hand and arm are inserted through the hole (which stretches to the extent needed to accommodate the arm), the elastic material cuff seals tightly around the arms of the health care worker. It can be understood that medical equipment could also be inserted through the holes in the elastic material and sealed therein, as well. Flaps, which may be of a pliable material, seal against the holes when not being used by the worker, to enable the pressure seal to be maintained.

A negative pressure fitting or connection is fixed to the hood for connection to the hospital suction source, to create a negative pressure environment within the hood. A portable negative pressure pump mount permits the hood to be used for negative pressure transportation of the patient.

Overall, the sealed hood permits creation of a sealed, negative pressure environment around a patient's head and upper body, while still enabling health care personnel to work within the hood via openings in the elastic material in the access openings. Any pathogens emitted from the patient are pulled into the hospital suction and the healthcare workers are isolated from same. It is understood that the apparatus creates what is essentially a loose seal about the patient, which permits some air to enter the interior of the hood in response to the negative pressure, but which stops air flow out of the hood.

In addition to intubation procedures, the apparatus may be used for other medical respiratory treatment, for example long term intensive care unit (ICU) patients, thereby saving PPE and preventing spread of contaminants. Sealed side port holes may be provided for ventilator and feeding tube passage. It is understood that the scope of the invention comprises any medical treatment which can be accomplished by use of the system.

Contoured edges are provided as necessary to avoid sharp edges and pressure hot spots for the patient.

The hood, at least portions thereof, is advantageously formed from clear materials, including but not limited to plastic, for example PETG (polyethylene terephthalate glycol), which can be shaped as desired. This permits viewing of the patient under the hood. Preferably, the hood is of unitary construction with rounded surfaces, particularly on the inner surfaces joining the sides and top, eliminating sharp corners of plexiglass hoods which are difficult to clean and disinfect. The rounded surfaces of the instant hood are much easier to clean and disinfect. The hood can be shaped in the form by methods known in the art.

Preferably, the system comprises controls and instrumentation to monitor air flow into and out of the hood interior, and to monitor the pressure differential between the interior of the hood and the ambient surroundings. A loss of the pressure seal, hence creation of a possibility of pathogens flowing from the interior of the hood, may give rise to an alarm based on either or both of pressure and airflow readings.

Preferably, a plurality of pathogen-killing lights, such as ultraviolet-C (UV-C) lights, are mounted on or around the hood, with the light directed inside the hood, to kill pathogens such as virus, including but not limited to COVID-19 virus.

DESCRIPTION OF THE PRESENTLY PREFERRED EMBODIMENT(S)

While various negative pressure respiratory treatment hoods can embody the principles of the present invention, with reference to the drawings some of the presently preferred embodiments can be described. It is understood that certain of the elements are not shown in all of the drawings, for clarity.

Figure 4:
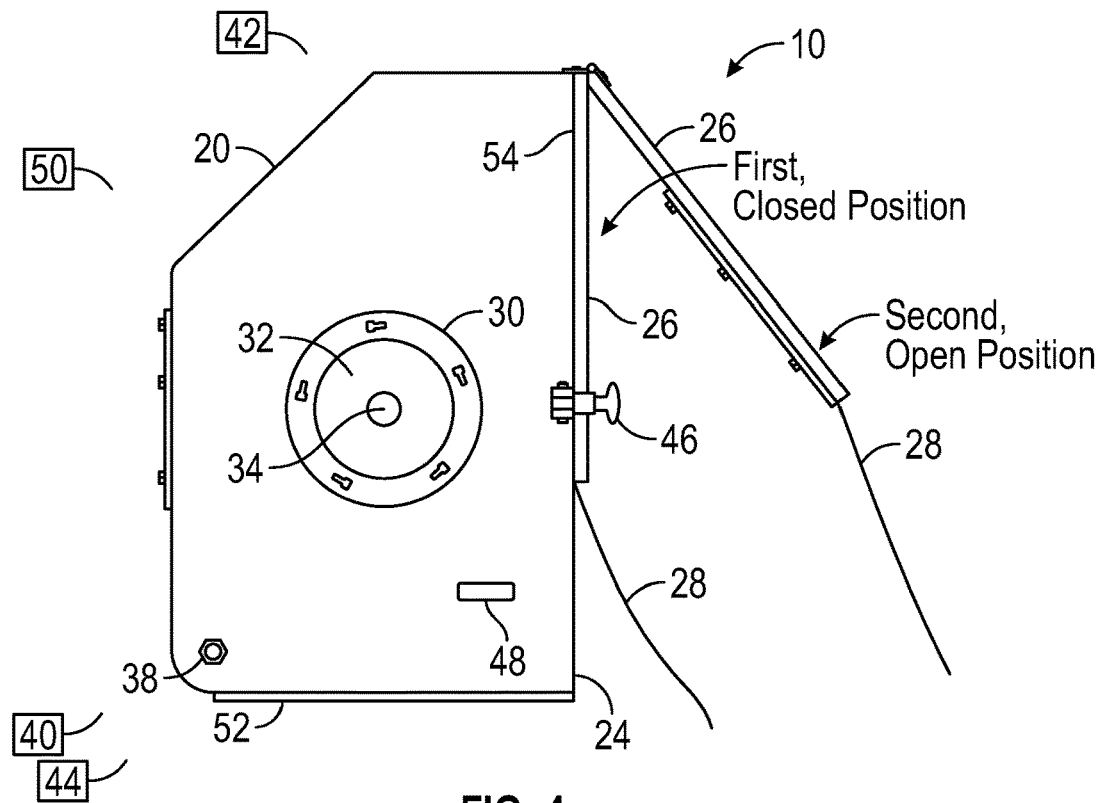
FIG. 4 is a side view of the hood (side wall).
Figure 5:
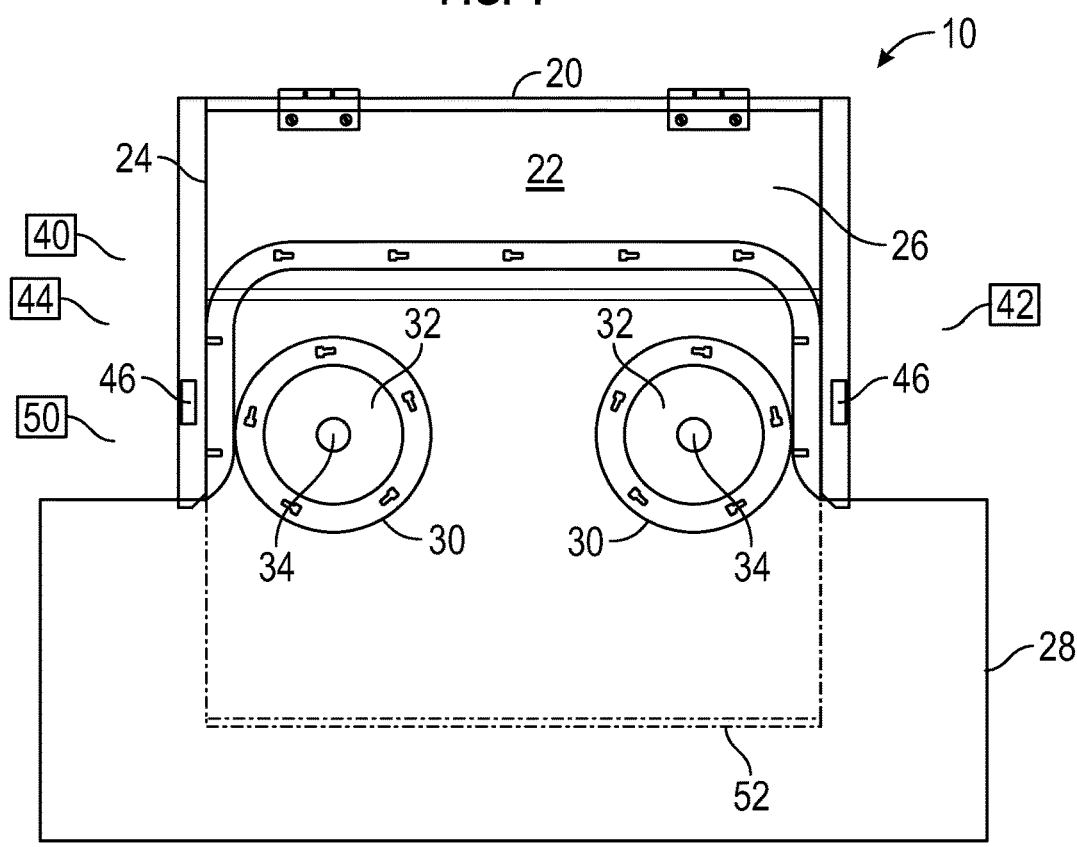
FIG. 5 is a side view of the hood, showing the door side (front wall).

The negative pressure respiratory treatment hood system 10 embodying the principles of the present invention comprises a generally box-shaped rigid hood 20 with an opening 22 in a front wall 24 to receive the head, and preferably at least a portion of the neck and shoulders, of a patient to be treated, for example intubated. At least portions of hood 20 are made of a material which is sufficiently transparent that the patient within the hood can be viewed therein, therefore permits the health care personnel to see into the interior of hood 20, so as to enable treatment of the patient; as noted below, in a preferred embodiment hood 20 is formed from a substantially transparent material, for example only a clear plastic, as described in more detail below. The patient would typically be on his/her back on a table, face up, and hood 20 is placed in position over the patient's body. In a presently preferred embodiment, a hinged door 26 is attached to an upper edge of opening 22 and movable between a first, open position (as can be seen in FIG. 4), to permit easier placement of hood 20 around the patient; and a second, closed position, as in FIGS. 1 & 2, rotated down toward or around the patient's body. However, it is understood that door 26 may or may not be provided. If provided, door 26 preferably has a cut-out shape, preferably to fit the general shape of the patient's body, as can be seen in FIGS. 2 and 5, with a shroud 28 (shown in FIGS. 1, 2, 4 and 5) to fit tightly around the patient's body and provide a seal. Shroud 28 may be made from an elastic material such as rubber or the like. Shroud 28 may be held tightly in place by fasteners, such as cleats 48 or similar means. Latches 46 may be provided to hold door 26 in the closed position.

Figure 1:
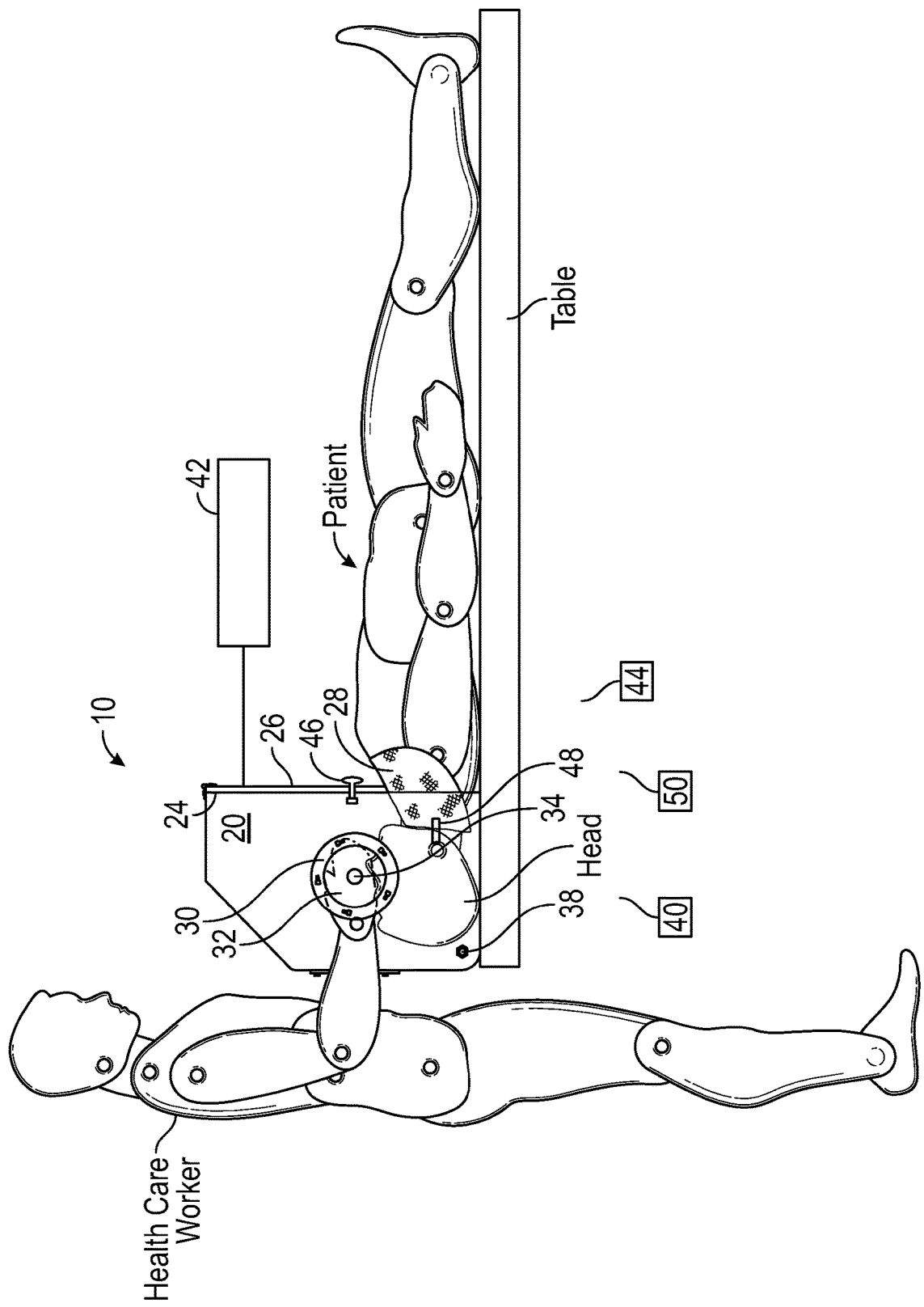
FIG. 1 is a side view one embodiment of the negative pressure respiratory treatment hood system (at times referred to as the "hood"), showing a patient in position and a health care worker in an exemplary position with hands and arms inserted into the interior of the hood for carrying out a procedure on the patient.
Figure 2:
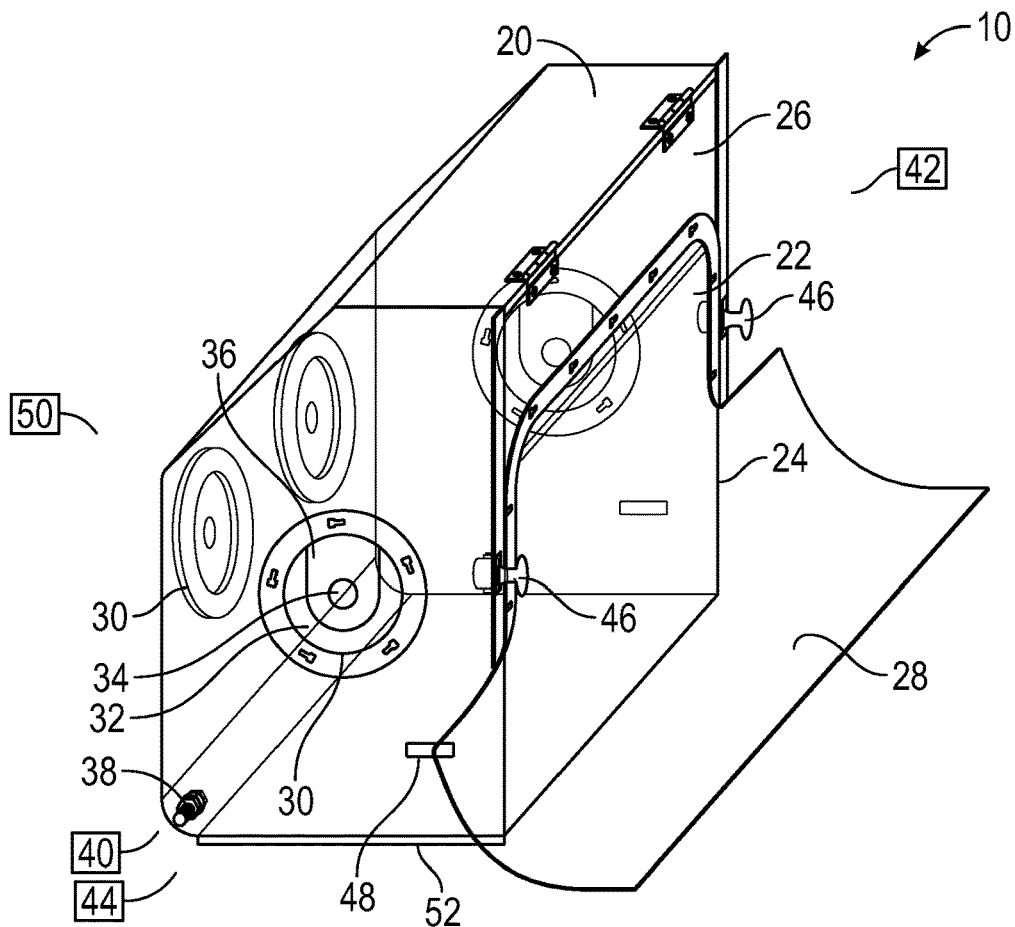
FIG. 2 is a perspective view of the hood.
Figure 3:
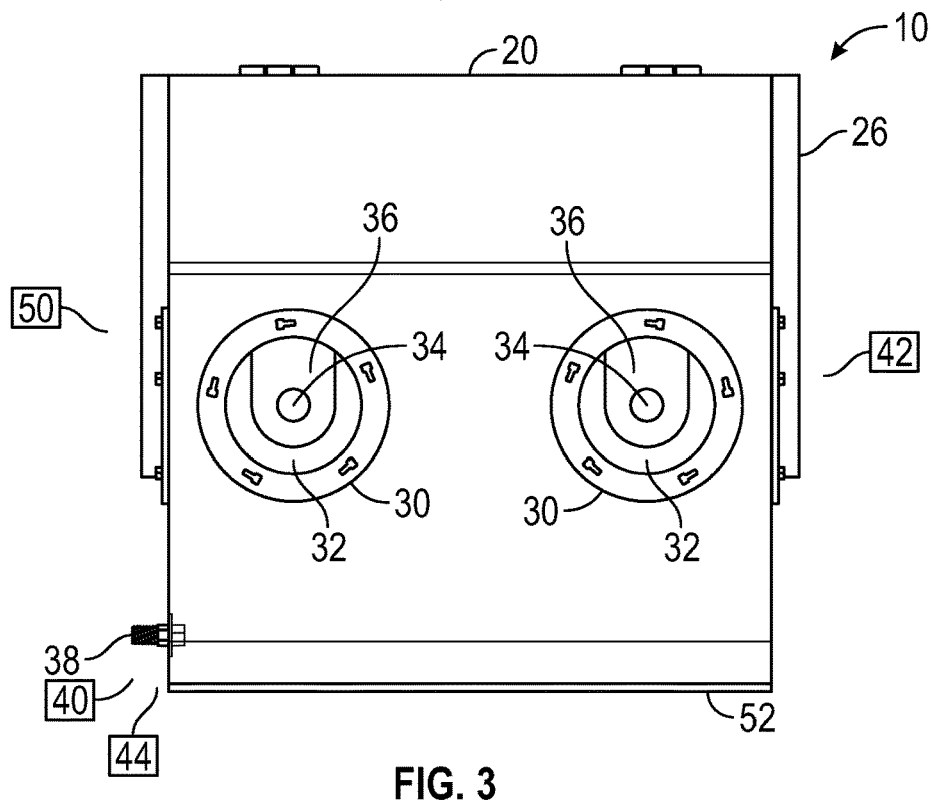
FIG. 3 is a side view of the hood, namely the front side away from the door (rear wall).

One or more access openings 30 are provided in the walls of hood 20 to permit access to the interior of hood 20, and thus the patient, by healthcare workers, as can be seen in FIG. 1. It is understood that any number of access openings 30 may be provided, in order to efficiently access the patient and/or manipulate instruments within hood 20. Each access opening 30 is covered by an elastic material 32, for example a highly stretchable rubber shroud or cuff, having an opening 34 therein. Opening 34 is preferably small in diameter (relative to the diameter of access opening 30) and centrally positioned in elastic material 32. The health care worker inserts his or her hand, then arm, through opening 34, into the interior of hood 20, with elastic material 32 sealing tightly around the arm and maintaining the negative pressure seal. Flaps 36 are shown in FIG. 3, are preferably provided over each of openings 34, and cover openings 34 when not in active use, thereby maintaining the negative pressure seal within hood 20. It is understood that flaps 36 essentially work as check valves. In a preferred embodiment, flaps 36 may be made of a flexible or pliable sheet of material, which in a first position are covering openings 34, and can be simply bent back out of the way to permit access through openings 34.

A connection 38, namely a negative pressure fitting, shown in FIGS. 1-4, is fixed to the hood for connection to the hospital suction or vacuum source 40, to create a negative pressure environment within the hood. In addition, a portable negative pressure pump 44 can be attached to permit movement of the patient while maintaining the negative pressure environment.

In a presently preferred embodiment, measurement and instrumentation devices are provided to monitor both air flow rate into and out of the interior of hood 20, and to monitor a pressure differential between the interior of hood 20 and ambient pressure outside of hood 20. Alarms are provided to signal undesired flow and/or pressure differential conditions. The measurement, instrumentation and alarms are represented schematically as element 50 in the drawings.

A bottom seal 52 can be added to the bottom surface of hood 20, and a door seal 54 can be added between door 26 and hood 20.

FIG. 3 is a view from the direction of the position of the health care worker in FIG. 1.

FIG. 4 is a side view, showing door 26 and attached shroud 28 in a first, closed position and in a second, partially opened position, as noted.

FIG. 5 is a view of the system looking into opening 22, with door 26 in a closed position and shroud 28 in a flattened position.

Figure 6:
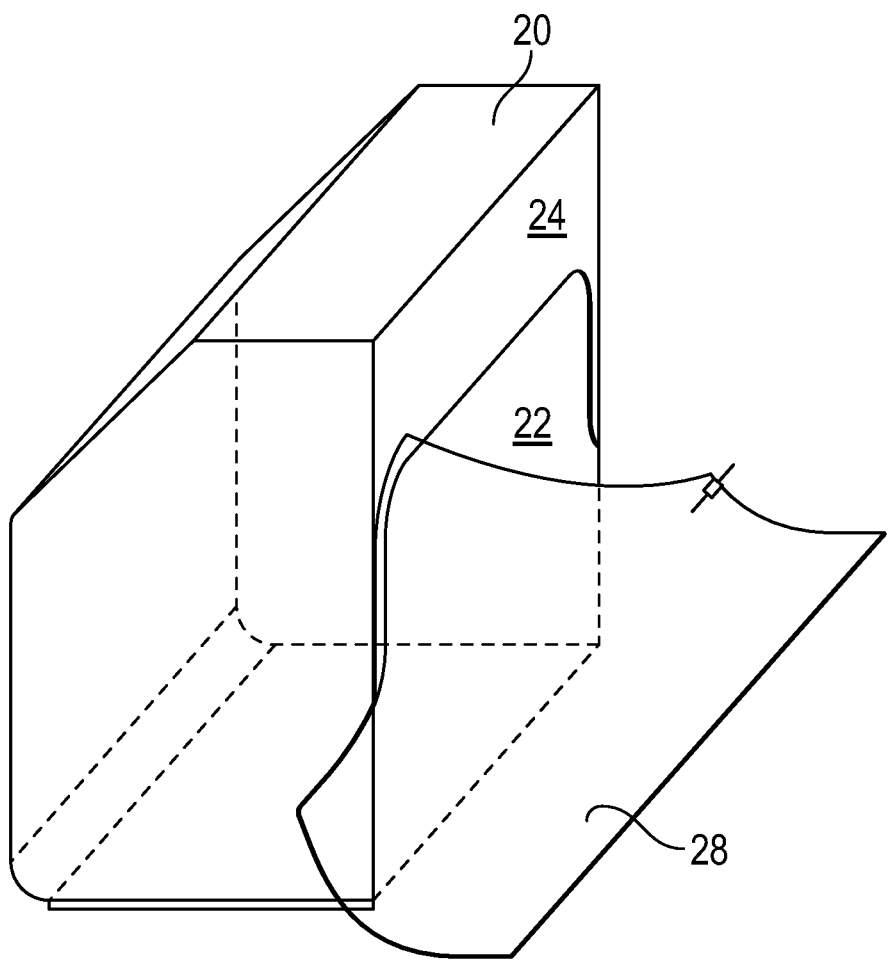
FIG. 6 is a perspective view of an embodiment of the hood 20 without the attached door, and showing the hood shroud in partial view. Various other elements of the system are omitted from FIG. 6, for clarity.

FIG. 6 is a perspective view of an embodiment of hood 20 without door 26, and showing shroud 28 in partial view. Various other elements of the system are omitted from FIG. 6, for clarity.

Overall, the system 10 permits creation of a sealed, negative pressure environment around a patient's head and upper body, while still enabling health care personnel to work within the hood via the rubber shrouds in the access openings. It is to be understood that the sealed, negative pressure environment may be regarded as a "loosely sealed" environment, as air may flow into the interior of the hood in response to the negative pressure (vacuum) created therein, but air and any pathogens carried therein would not leave the interior of the hood. Any pathogens emitted from the patient are pulled into the hospital suction and the healthcare workers are isolated from same.

Preferably, a plurality of pathogen-killing lights, such as ultraviolet-C (UV-C) lights 42 are mounted on or around the hood, with the light directed inside the hood, to kill pathogens such as virus, including but not limited to COVID-19 virus. UV-C lights (emitting light with a wavelength generally between 200 and 280 nm) have been shown to have effective germicidal properties. It is understood that other pathogen-killing lights may be used.

A Method of Use of the System

An exemplary method of use of system 10, to create a negative pressure environment around the head of a human medical patient and carrying out a medical procedure within said negative pressure environment, may comprise the steps of:

a) positioning the human medical patient upon a table;
b) placing a rigid hood over the medical patient so as to receive the medical patient's head within an interior space of the rigid hood, at least a portion of said hood being sufficiently transparent that the medical patient within said hood can be viewed inside the hood, the rigid hood comprising walls and comprising an opening in a front wall with the medical patient's body extending through said opening;

c) draping a shroud over the patient's body and securing the shroud to the hood, the shroud creating at least a partial pressure seal around the patient's body; and d) connecting a negative pressure source to said interior of said hood and creating a negative pressure environment inside the hood.

Commonly, a method of use would also include the step of:

e) accessing the medical patient within the hood and performing a desired medical procedure on the patient, the access being through one or more access openings in the walls of the hood, each of the one or more access openings covered by an elastic material having an opening, the elastic material and the opening therein permitting access to the medical patient while maintaining a negative pressure environment within the hood, the hood comprising a flap which bears against the opening in the elastic material and forms a pressure seal against same, the flap being movable to permit access through the opening in the elastic material.

Materials and Fabrication

Hood 20 is advantageously formed from a clear or largely clear material, which may be a plastic, such as PETG (polyethylene terephthalate glycol), which can be shaped within a hemispherical form, and forms a rigid hood 20. It is understood that any other material of sufficient transparency may be used to fabricate hood 20. Preferably, hood 20 is of unitary construction with rounded surfaces, particularly on the inner surfaces joining the sides and top, eliminating sharp interior corners which are difficult to clean and disinfect. The rounded surfaces of the hood 20 are much easier to clean and disinfect. Hood 20 can be shaped in the form by methods known in the art. The elastic material (for example, rubber or the like) shrouds and access opening material may be of materials known in the medical arts. It is understood that materials and methods of fabrication may be altered as desired.

Contoured edges are provided as necessary to avoid sharp edges and pressure hot spots for the patient.

CONCLUSION

While the preceding description contains many specificities, it is to be understood that same are presented only to describe some of the presently preferred embodiments of the invention, and not by way of limitation. Changes can be made to various aspects of the invention, without departing from the scope thereof.

Therefore, the scope of the invention is to be determined not by the illustrative examples set forth above, but by the appended claims and their legal equivalents.

We claim:

1. An apparatus, comprising:
   a rigid hood comprising walls, an opening in a front wall, and a size and shape designed to receive a patient's head within an interior space of said hood, when said patient is lying prone, at least a portion of said hood being sufficiently transparent that a said patient within said hood can be viewed therein;
   a shroud attached to said hood, said shroud shaped and dimensioned to drape over a said patient's body when said patient's head is positioned within said hood and said patient's body is extending through said opening in said front wall, said shroud creating at least a partial pressure seal around said patient's body;
   one or more access openings within said walls of said hood of sufficient size to permit access by a health care worker into said interior space of said hood, each of said one or more access openings covered by an elastic material having an opening therein, said elastic material opening and said elastic material permitting said health care worker to access said interior space of said hood while maintaining a pressure seal around said health care worker's body or medical equipment;
   a hinged door mounted proximal said opening in said front wall, said hinged door movable between a first, closed position and a second, open position, wherein said hinged door in said first closed position partially closes said opening;
   a flap which bears against said opening in said elastic material and forms a pressure seal against same, said flap being movable to permit access through said elastic material opening; and
   a connection for attachment of a negative pressure source to said interior space of said hood.

2. The apparatus of claim 1, wherein when a patient is positioned within said hood and a negative pressure source connected thereto, a negative pressure environment is created within said hood.

3. The apparatus of claim 2, further comprising pathogen-killing lights directed toward an interior of said hood.

4. The apparatus of claim 3, wherein said pathogen-killing lights are UV-C (ultraviolet C) lights.

5. The apparatus of claim 2, wherein said hood is designed to additionally receive a portion of said patient's upper body therein.

6. The apparatus of claim 1, further comprising pathogen-killing lights directed toward an interior of said hood.

7. The apparatus of claim 6, wherein said pathogen-killing lights are UV-C (ultraviolet C) lights.

8. The apparatus of claim 1, wherein said hood is designed to additionally receive a portion of said patient's upper body therein.

9. The apparatus of claim 1, further comprising a portable vacuum pump attached to said negative pressure source connection.

10. The apparatus of claim 1, further comprising:
    one or more latches to secure said hinged door in said first, closed position;
    a seal positioned between said hinged door and said hood; and
    a seal positioned on a bottom surface of said hood.

11. The apparatus of claim 10 wherein said shroud is of an elastic material, and further comprising fasteners to hold said shroud to said hood and securely against said patient's body.

12. The apparatus of claim 1, wherein said hood is formed from clear plastic.

13. The apparatus of claim 12, wherein said clear plastic comprises PETG (polyethylene terephthalate glycol).

14. A negative pressure respiratory treatment hood system, comprising:
    a rigid hood of unitary construction comprising front, rear, and side walls and formed from a substantially clear material, said rigid hood comprising rounded inner surfaces joining said walls, forming an interior space with a size and shape designed to receive a patient's head within said interior space when said patient is lying prone, said rigid hood comprising an opening in said front wall;
    a hinged door mounted proximal said opening in said front wall, said hinged door movable between a first, closed position and a second, open position, wherein said hinged door in said first closed position partially closes said opening, said system further comprising one or more latches holding said hinged door sealed against said hood in said first, closed position;

a shroud attached to said hood, said shroud shaped and dimensioned to drape over a patient's body when said patient's head is positioned within said hood and said patient's body extends through said opening in said front wall, said shroud being releasably attachable to said walls of said hood, said shroud creating at least a partial pressure seal around said patient's body;

one or more access openings within said walls of said hood of sufficient size to permit access by a health care worker into said interior space of said hood, each of said one or more access openings covered by an elastic material having an opening therein, said opening in said elastic material and said elastic material permitting said health care worker to access said interior space of said hood while maintaining a pressure seal around said health care worker's body or medical equipment;

a flap which bears against said opening in said elastic material and forms a pressure seal against same, said flap being movable to permit access through said opening in said elastic material; and a connection for attachment of a negative pressure source to said interior space of said hood.

15. The system of claim 14, further comprising a portable vacuum pump attached to said negative pressure source connection.

16. The system of claim 14, wherein said substantially clear material comprises PETG (polyethylene terephthalate glycol).

17. The system of claim 14, further comprising measurement and instrumentation devices to monitor both air flow rate into and out of said interior space of said hood, and to monitor a pressure differential between said interior space of hood and an ambient pressure outside of said hood.

18. A method of creating a negative pressure environment around the head of a human medical patient and carrying out a medical procedure within said negative pressure environment, comprising the steps of:

a) positioning said human medical patient upon a table;

b) placing a rigid hood over said medical patient so as to receive said medical patient's head within an interior space of said rigid hood, at least a portion of said hood being sufficiently transparent that said medical patient within said hood can be viewed therein, said rigid hood comprising walls and comprising an opening in a front wall with said medical patient's body extending through said opening, said rigid hood further comprising a hinged door mounted proximal said opening in said front wall, said hinged door movable between a first, closed position and a second, open position, wherein said hinged door in said first closed position partially closes said opening, said system further comprising one or more latches holding said hinged door sealed against said hood in said first, closed position;

c) draping a shroud over said patient's body and securing said shroud to said hood, said shroud creating at least a partial pressure seal around said patient's body; and d) connecting a negative pressure source to said interior space of said hood and creating a negative pressure environment therein.

19. The method of claim 18, comprising the additional step of:

e) accessing said medical patient within said hood and performing a desired medical procedure thereon, said accessing being through one or more access openings in said walls of said hood, each of said one or more access openings covered by an elastic material having an opening, said elastic material and said opening therein permitting access to said medical patient while maintaining a negative pressure environment within said hood, said hood comprising a flap which bears against said opening in said elastic material and forms a pressure seal against same, said flap being movable to permit access through said opening in said elastic material.

* * * * *